United States Patent [19]

Diesso

[11] Patent Number: 5,503,552
[45] Date of Patent: Apr. 2, 1996

[54] DENTAL IMPRESSION METHOD AND COMPOSITION

[76] Inventor: Michael Diesso, P.O. Box 648, E. Wareham, Mass. 02538

[21] Appl. No.: 154,177

[22] Filed: Nov. 18, 1993

[51] Int. Cl.$^6$ ...................................................... A61C 9/00
[52] U.S. Cl. ................................ 433/37; 433/48; 433/71; 433/214
[58] Field of Search ................................ 433/37, 48, 214, 433/71; 128/861, 862

[56] References Cited

U.S. PATENT DOCUMENTS

| | | |
|---|---|---|
| 3,312,218 | 4/1967 | Jacobs . |
| 4,472,140 | 9/1984 | Lustig . |
| 4,867,680 | 9/1989 | Hare et al. . |
| 5,011,407 | 4/1991 | Pelerin . |
| 5,051,476 | 9/1991 | Uji et al. ................................ 525/186 |
| 5,059,120 | 10/1991 | Lee . |
| 5,066,231 | 11/1991 | Oxman et al. . |

OTHER PUBLICATIONS

Polyvinyl Acetate, Union Carbide Polyvinyl Acetate Resins for Coatings and Adhesives, 2 pages.
ACPolyethylenes, Technical Data Sheet, A–C 430 Copolymer.
Allied Signal Product Safety Data Sheet, Actol Resin Modifiers, 2 pages.
Modern Plastics Mid–October Encyclopedia Issue, Introduction to Branched PE, pp. 67–74.
Elvax 200 Series Resins—12 pp.
Elvax Resins for Molding, Compounding and Extrusion 6 pages.
Actol Technical Data for Coatings, Resin Modifiers in Power Coatings pp. 2–8.
Actol Technical Data for Coatings, Resin Modifiers in Water–Borne and Solvent–Based Coatings 8 pages.

*Primary Examiner*—Nicholas D. Lucchesi
*Attorney, Agent, or Firm*—Laff, Whitesel, Conte & Saret, Ltd.

[57] ABSTRACT

A dental impression composition, dental impression pre-form and/or pre-mold and method for taking a dental impression that includes a pre-form made of an ethylene vinyl acetate copolymer mixed with a second polymer selected from vinyl acetate, a second ethylene vinyl acetate and a vinyl acetate vinyl alcohol ester. The pre-form softens at a temperature of about 120° F. to 170° F. The composition and method may also include a second pre-form made of a thin separator film sheet of a high molecular weight polycaprolactone, sandwiched between two ethylene vinyl acetate pre-forms.

51 Claims, 3 Drawing Sheets

DENTAL IMPRESSION METHOD AND COMPOSITION

FIELD OF THE INVENTION

The present invention relates to a dental impression method and composition. More particularly, this invention relates to a method for preparing dental impression molds and to the dental impression composition thereof.

BACKGROUND OF THE INVENTION

A variety of devices for making dental impressions of a patient's teeth are known. The term "dental impression" is used in the dental trade to designate a specific functional object and is distinguishable from the more general term "impression". Specifically, a dental impression provides a mold which is, in essence, an exact replica of the reverse image of a dental arch or arches or area of a dental arch. A dental impression is classified as full arch upper maxillary, full arch lower mandibular, anterior, quadrant, or bite registration. Dental impression focuses on the precise size and position of the teeth, the gingival tissues, and any surgical alterations so that a working model may be produced. It is on this working model that a dental prosthetic device will be fabricated for eventual insertion into the mouth of a dental patient.

The material used for making dental impressions must satisfy specific requirements established by the American Dental Association (ADA), Council on Dental Materials (Revised Specification No. 19 for Non-Aqueous, Elastomeric Dental Impression Materials). A copy of Revised Specification 19 is enclosed with this application and is incorporated herein by reference. Specifically, the ADA requires that elastomeric dental impression materials have a certain dimensional integrity, elastomeric distortion limit, recovery rate, detail capturing capabilities, as well as other physical parameters. Specifically, non-aqueous elastomeric dental impression materials are classified according to their elastic properties and dimensional change after "setting". Each type is further classified according to its apparent viscosity and intended use. Likewise, the aforementioned working model must fulfill specific requirements related to accuracy and hardness.

A number of dental impression devices, processes and/or the compositions are known. While these known dental devices, processes, and compositions provide a means for dental impressioning, there are certain disadvantages associated with their use. One such disadvantage is that these known processes generally require the use of a dental impression tray. These impression trays are made of various stock or custom made sizes to accommodate the specific type of dental impression desired. Furthermore, some of these dental impression processes involve a pre-step prior to the actual impression step. In addition, although several of the known dental impressioning processes allow for two or more types of dental impressions to be taken at the same time, such methods generally require the use of an impression tray and/or a time-consuming pre-step prior to the actual impression step.

Presently, the predominant use is with three elastomeric dental impression materials used with impression trays and in other related dental impression procedures. These three materials are polysulfides, silicones, and polyethers. Each of these materials involves the previously mentioned pre-step or two-part chemical reaction cure system that is costly, time-consuming to implement, and subject to shelf-life age changes. Furthermore, each of these materials are messy to work with and require a clean-up phase following their use. Additionally, due to the nature of cure for each of these materials, they are said to be thermoset. In other words, once these materials have reacted, they are permanently changed and cannot be used again. This creates a great expense for the dentist who frequently does not obtain a suitable impression of the teeth or tissues to his/her satisfaction as a result of, for example, a gagging patient, and must redo the impression which involves using new material, a new impression tray, and an additional mess.

Generally, each of the dental impression materials are mixed to a pasty consistency and placed into an impression tray that acts as a carrier. The filled impression tray is placed and pressed into the patient's mouth. The procedure and the materials used generally create a time consuming clean-up.

Furthermore, present dental impression techniques which provide for multiple types of dental impressions at one time generally involve the use of an impression tray and a pre-step prior to the dental impression step. In addition, these same dental impression techniques are used to make master models from which functional dental devices are designed. For example, master models are presently used for fabricating tempro-mandibular joints, bruxism or night guards, anti-snore devices, denture relines, mouth guards, retainers or bite risers, and other similar functional dental devices. Such devices essentially differ from one another in the materials or material formulas used for their construction, their intended purpose, and the method of their construction.

Some of the patents which implement these materials and/or involve the use of impression trays are described in U.S. Pat. Nos.: 4,472,140; 4,867,680; 5,011,407; 5,059,120; 5,066,231. These patents show that dental impression trays are made of various stock or custom made sizes for accommodating the specific type of dental impression material desired. In addition to the foregoing, U.S. Pat. No. 3,312,218 discloses an impressionable mouth protector. Each of the aforementioned patents is described in greater detail below.

U.S. Pat. No. 5,066,231 discloses the use of a blend of high and low molecular weight polycaprolactone for use as a dental impression material. As a practical matter, the use of this material would be very limited to edentulous arches (no teeth) due to its inherent stiffness, inability to flex out from undercut areas, and inability to avoid entrapment in interproximal spaces.

U.S. Pat. Nos. 4,472,140 and 5,059,120 disclose dental impression tray devices with various waxes, zinc-oxide eugenol pastes, silicone, plastics, self cured and light cured resins that are used in conjunction with film, gauze, and strips which act as separation layers. The impression tray device in the '140 patent carries the wax impression material to the patient's mouth. In addition, the '140 patent describes a method of acquiring multiple types of dental impressions at one time. For example, impressions may be simultaneously taken of upper teeth, lower teeth, and the bite registration. A foraminous film serves as a thin separator inside a metal or plastic frame which serves as the carrier of the dental impression material.

U.S. Pat. No. 4,867,680 discloses a dental impression tray device which uses a polymerizable preferably light cure impression material that includes various acrylates.

U.S. Pat. No. 5,011,407 discloses making a custom dental impression tray that is fabricated from polycaprolactone. The patient bites into a softened pre-formed piece of the material to register position of the teeth in the tray for a closed bite impression. The tray assembly is molded around the affected areas of the mouth and allowed to harden. A wax spacer layer is removed and the tray is then filled with dental impression material in the space where the wax was, such as silicone, and reinserted into the patient's mouth for the impression procedure.

U.S. Pat. No. 3,312,218 discloses a mouth protector which is made from a vinyl resin comprising an ethylene vinyl acetate copolymer, such as Elvax 250. Elvax 250 is typically used in paraffin wax systems where viscosity limitations are less stringent or where higher viscosities are required.

Thus, while the aforementioned patents disclose a variety of devices and methods for dental impressioning, there are still some problems associated with their use.

Accordingly, an object of the present invention is to provide a method and composition for dental impressioning that is convenient and easy to use.

Other objects and advantages of the invention will appear hereinafter.

SUMMARY OF THE INVENTION

The present invention accomplishes the foregoing objects by providing a method and composition for dental impressioning. In one embodiment, a pre-form is made from heat and sheer treated ethylene vinyl acetate copolymer having from about 30% to about 45% by weight vinyl acetate. The copolymer is subjected to extrusion wherein the copolymer is subjected to high shear forces under melt and forced by back pressure through the screw and formed into sheets, strips, rods, ropes, blocks, buttons, bars, pellets, or channel profiles. The melt processing under pressure of the copolymer has an effect on the copolymer that is not completely known. There has been some conjecture that such a process in some manner may alter the molecular weight of the copolymer. In any event, the heat and pressure treatment of the ethylene vinyl acetate copolymer compositions appears to substantially reduce or eliminate the memory characteristics of the copolymer such that it can be softened at a temperature of from about 120° F. to about 170° F. and be used to take dental impressions that will remain accurate when the copolymer is cooled. The treated material provides a dental impression material whose detail capturing ability and dimensional accuracy are such that a greater number of different types of dental impressions may be accomplished.

In the preferred embodiment, the pre-form is made from a treated composition containing the ethylene vinyl acetate copolymer and a modifier. The preferred modifiers are vinyl acetate, a second ethylene vinyl acetate, polyvinyl acetate, ethylene vinyl acetate hydroxyl compound with at least one esterified hydroxyl compound and mixtures thereof. The preferred modifiers are the second ethylene vinyl acetate having a vinyl acetate content of 23–30% by weight and an ethylene vinyl acetate vinyl alcohol having at least one esterified hydroxyl group and mixtures thereof. The modified ethylene vinyl acetate composition may be formed by melt blending the ethylene vinyl acetate copolymer with the modifier and the resulting melt blended composition being molded or extruded to prepare the desired form of the dental impression material.

In an embodiment for taking upper and lower dental impressions at the same time, I provide a dental impression pre-form which has a thin separator film sheet made of a high molecular weight material, such as polycaprolactone, sandwiched between formed sheets of treated ethylene vinyl acetate copolymer which is first melted and extruded or molded into a pre-form in the form of sheets, strips, rods, ropes, blocks, buttons, bars, pellets, or channel profiles. Then two pieces of the copolymer pre-form are combined with the second pre-form material by selectively sandwiching the second or polycaprolactone pre-form between a top and bottom sheet of the ethylene vinyl acetate pre-form. The polycaprolactone pre-form is preferably processed into a pre-form which matches the ethylene vinyl acetate pre-form. The polycaprolactone pre-form functions as a thin film separator that softens comparably to the ethylene vinyl acetate preform, i.e., at a temperature of about 120° F. and preferably about 130° F.

Specifically, the ethylene vinyl acetate dental impression composition is in the form of sheets, strips, rods, ropes, blocks, buttons, bars, pellets, or channel profiles. If the ethylene vinyl acetate dental impression material is not already in ready-to-use sheet pre-form, the rods etc. may be melted and molded into ready-to-use form. Then a second pre-form material is sandwiched between two pieces of the ethylene vinyl acetate pre-form. Both the pair of first pre-forms and/or the second pre-form are heated to a sufficient non-deforming temperature that causes the first and second pre-forms to adhere to each other to form a two-sided dental impression device which acts as two-sided dental impression pre-mold. The polycaprolactone pre-form is preferably processed into a pre-form which matches the ethylene vinyl acetate dental impression pre-form. The polycaprolactone pre-form functions as a thin film separator that softens comparably to the ethylene vinyl acetate pre-form.

The two-sided dental impression pre-mold is then placed into a container of hot water having a temperature of about 150° F. to 180° F. for a short period of time, i.e., 30 to 300 secs. to soften the premold. The pre-mold, which has retained its general shape and conformation, is then removed from the water and placed into and broadly on the occlusal surface of the lower teeth of the patient's mouth. The patient is then instructed to close into a normal centric occlusion and instructed to hold this position for a designated time period, usually about 5 minutes and less than 10 minutes. At the end of this time, the dentist may remove the dental-impression mold from the patient's mouth, revealing a highly detailed and accurate dental impression of the upper teeth, the lower teeth, and the bite registration.

The dentist may now use the mold by taking a model material, such as gypsum, to fill the irregular surfaces in the depression. The filling of the irregular surfaces in the dental impression with a model material is facilitated by the polycaprolactone membrane which separates and segregates the upper teeth mold from the lower teeth mold. The polycaprolactone membrane or separator conforms precisely to the irregularities of the occlusal surfaces while simultaneously cooling to form a barrier for separating the upper portion from the lower portion of the impression. Thus, when the upper portion of the impression is being filled with gypsum to form an upper model, it remains totally segregated from the lower impression. The lower chamber of the impression can then in turn be filled with gypsum without making contact with the upper chamber, and yet the bite relationship is preserved.

The model material is used to make working models of the patient's arches for the purpose of appliance or dental prosthetic device fabrication.

In those embodiments in which the polycaprolactone pre-form is not present, the ethylene vinyl acetate dental impression pre-mold may be used for several purposes in dentistry, including: one, as a matrix for determining the correct alignment of the upper and lower teeth after models have been produced and require indexing for articulation; two, as a functional dental impression device that itself will serve and function as the treatment device, such as, for example, a tempro-mandibular joint splint, a bruxism or night guard, a retainer, a bite riser, an anti-snore device or for maintaining a specific position of the upper and lower teeth and their relationship to each other, as determined by the dentist or patient; three, as a victim identification in forensic sciences; and four, as a check bite or matrix in the procedure for relining or rebasing dentures.

In the last above-described embodiment or in that embodiment wherein the polycaprolactone pre-form is present, the dental impression may be used for several purposes in dentistry, including: one, as a dental impression for fixed restorative; two, as a dental impression for removable partial dentures; three, as a dental impression for orthodontic diagnostic casts or appliance fabrication; and four, as a dental impression for production of general purpose diagnostic casts, or for reproduction of master casts.

In each of the above-mentioned embodiments, if there is an area of surgical alteration on one or more of the teeth that was not captured correctly due to, for example, a gagging patient, or to the satisfaction of the dentist, the pre-form material may be selectively re-heated with a pin point torch or flame precisely in one specific area for re-softening the material. The impression may then be reseated to recapture and perfect a specific area. This may alternatively be accomplished by adding extra resoftened material to a specific area of deficiency, or by adding an alternative material for relining a specific area of deficiency or inadequacy.

Thus, the method and composition for dental impressioning disclosed herein relates broadly to a pre-form that does not require a separating film and is a functional dental impression used primarily as a tooth position device, assist, or relator; and to a pre-form pre-mold that preferably uses a separating film so that when the dental impression mold is formed, it may be filled with a gypsum material for fabricating working models and oral prosthetic devices. Both of the above embodiments include sub-embodiments which are directed to variations in the materials used to make the pre-forms. All of the embodiments eliminate the need for a dental impression tray. However, it should be understood that any of the pre-form blends could be used in a conventional manner such as placing the material into a dental impression tray like any other dental impression material. Because the inventive pre-form material herein does not need to be mixed or combined from multiple parts to effect a cure, it may be pre-loaded into disposable dental impression trays of various sizes. These pre-loaded trays then need only to be placed into a container of water preferably at a temperature range of about 130° F. to about 170° F. for about one to two minutes and then inserted into the patient's mouth for conventional dental impressioning procedures.

In still another embodiment, the impression material may be preloaded or loaded into a syringe. When the dentist is ready to use the material, the syringe is heated to a temperature of about 150° F. to about 180° F. to soften the material to point where it can flow sufficiently to be ejected from the syringe into an appropriate dental impression tray.

The above, as well as other objects and advantages of the invention, will become apparent from the following detailed description of the preferred embodiments, reference being made to the accompanying drawings.

DETAILED DESCRIPTION OF THE INVENTION

Figure 1:
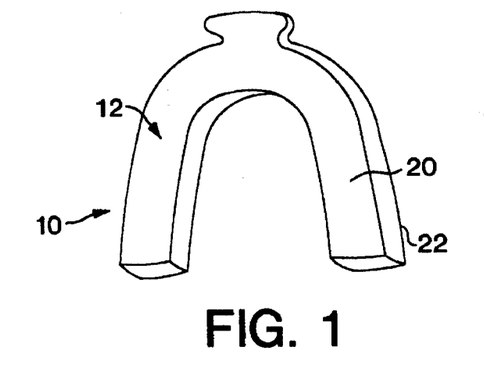
FIG. 1 is a perspective view of the preferred embodiment of the inventive dental impression.
Figure 2:
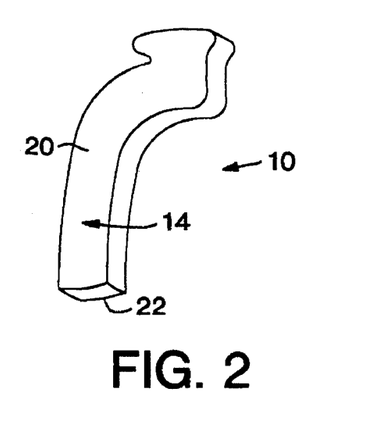
FIG. 2 is a perspective view of a quadrant bite registration made from the inventive dental impression material.

Generally the invention provides a method and composition for dental impressioning material comprising a vinyl acetate wherein the composition softens to an appropriate dental impression use at a temperature of from about 120° F. to about 170° F., and forms a rubber-like dental impression in a patient's mouth within three to eight minutes after being positioned in the patient's mouth. Referring to FIGS. 1 and 2, a dental impression pre-form, denoted by the numeral 10, is made of my dental impression material. Pre-form 10 is flat and semi-circular in shape and is approximately 3/16 inch thick. Pre-form 10 may be formed in a plurality of sizes and-shapes, such as a full bite registration 12 (FIG. 1) or a quadrant bite registration 14 (FIG. 2).

Figure 3:
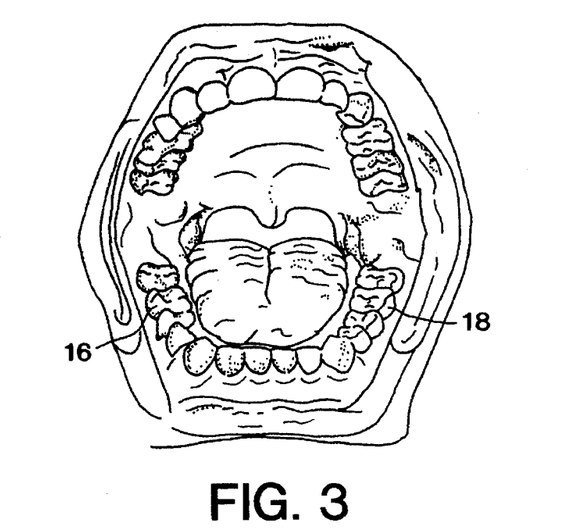
FIG. 3 is a fragmentary perspective view of the occlusal surface of the lower teeth of a patient.
Figure 4:
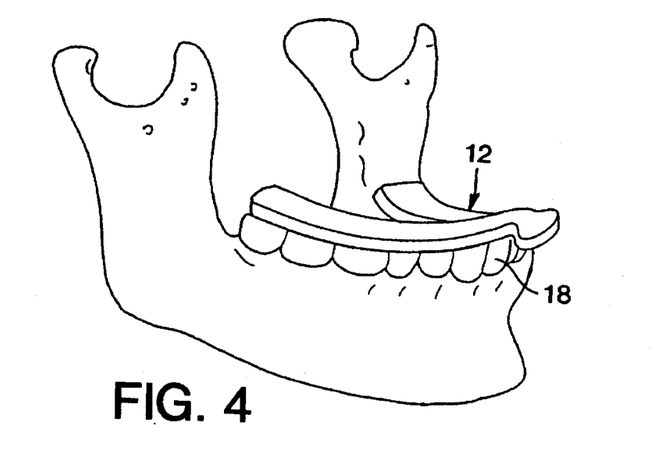
FIG. 4 is a perspective view of a human jaw, illustrating the inventive dental impression of FIG. 1 as it appears positioned on the occlusal surface of the lower teeth prior to an impression being taken.

The dental impression pre-form is placed into a container of water that is of a temperature range between 120° F. and about 180° F. and preferably about 150° F. to about 170° F. The pre-form is left in the hot water for approximately 30 seconds to about 3 minutes and preferably about one to two minutes and is then removed. Although there is no appreciable loss of form or shape, the material is now extremely soft. The soft dental impression pre-form is at such a temperature that it can easily and comfortably be placed onto the occlusal surface 16 (FIGS. 3 and 4) of the lower mandibular teeth 18 of the patient wherein the patient is instructed to close fully into a normal centric occlusion such that the upper and lower teeth firmly press against the upper and lower surface, 20 and 22, of the full bite registration 12 respectively, of the pre-form. The patient holds this position for about 4–6 minutes. At the end of this time, the pre-form is removed from the patient's mouth. The dental impression pre-form has now hardened into a non-distortable rubber-like dental impression which shows the upper teeth, the lower teeth, and the relationship of the upper and lower teeth to one another.

The dental impression pre-form is prepared from a vinyl acetate polymer composition that would fulfill the American Dental Association Specification No. 19 for dental impression materials. The vinyl acetate polymer pre-form, after being heated, has a minimum time for removal from the mouth of less than 10 minutes. The vinyl acetate polymer dental impression mold has a maximum negative change in dimension after 24 hours of less than 0.50 as measured by the 4.3.9 test set forth in the ADA specification. The dental impression mold is compatible with gypsum.

The dental impression pre-form is prepared from a vinyl acetate polymer that is hard at room temperature to about 110° F., is compatible with gypsum at room temperature, and softens at temperatures above about 120° F. and preferably above about 130° F. and moldable at temperatures of 170° F. The preferred dental pre-form has a vinyl acetate content of at least 15% by weight. The preferred vinyl acetate polymer is an ethylene vinyl acetate copolymer. Other ingredients may be included in the dental impression composition such as small amounts of colorants, clay and/or silica fillers which change the appearance of the material for sales and marketing appeal. The term "hard" as used above includes the rubber-like consistency set forth in the Examples.

One of the preferred ethylene vinyl acetate copolymers used is commercially available from DuPont Company and is known as Elvax grade 40W. Elvax 40W has a vinyl acetate content 39% to 42% by weight, an inherent viscosity of 0.70 g/ml, a melt index of 48 to 66 dg/min (ASTM D1238, modified), a hardness of 40 shore, and a softening point of 104° C. DuPont offers many different grades of ethylene vinyl acetate resins and classifies each according to the specific degree of toughness and durability desired for the finished goods. DuPont suggests using Elvax 40W for compounding adhesives, lacquers, wood primers and other solvent based formulations. Other DuPont Elvax grades are principally intended for wax blending, injection molding and extrusion with typical applications that include flexible hose and tubing, auto bumpers, footwear components, wire and cable, toys, athletic goods, and extruded gaskets.

In one embodiment, Elvax 40W is extruded in a pressure screw extruder having about a 3.5 inch diameter and a 3 to 1 compression at temperatures of about 180° C. to about 240° C. and formed into desirable sheets, rods, pellets, etc. The sheets, rods, pellets, etc. are preferably cut or formed into dental impression pre-forms. The extrusion softens and relaxes the memory on subsequent resoftenings of the pre-form. Although it may be possible to use Elvax 40W without subjecting it to extrusion, the extrusion greatly improves the processability of the material for use in dental impressioning procedures.

In a preferred embodiment, the dental pre-form is prepared from two separate types of ethylene vinyl acetates. For instance, a better dental impression pre-form is formed from a dental impression composition containing Elvax 40W and another ethylene vinyl acetate such as Actol and/or A-C polyethylene.

The preferred Actol is Actol 65 purchased from Allied Signal, Inc. The Actol 65 data sheet and literature shows that it has a formula of $(C_4H_6O_2)_x (C_2H_4O)_y (C_2H_2)_z$ and has the chemical name of ethylene vinyl acetate vinyl alcohol copolymer, has a melting range of 40°–65° C., hardness dmm (ASTM D-5) of 16.0–17.0, viscosity cps @ 140° C. Brookfield 1100, hydroxyl number (ASTM E22) of 85–120, equivalent weight of 465–660, and an average molecular wt of 2400.

The preferred A-C polyethylene is the AC polyethylene 400 series with 430 being preferred. This was also purchased from Allied signal and has a product name of ethylene vinyl acetate copolymer with a grease-like form with the vinyl acetate content being 23 to 30% by weight, the viscosity-cps @ 140° C. (Brookfield) of 600, having a hardness at 25° C.

of 40–100 dmm, a Metler drop point of 80° C. and a density of 0.93 g/cc.

The addition of the vinyl acetate copolymers Actol or A-C polyethylene to the Elvax 40W alters the physical properties of the Elvax 40W as evidenced by the resulting end products as follows. First, these two vinyl acetates reduce the temperature at which the Elvax 40W will soften. This is important because it prevents the possibility of burning of the oral tissues. Second, these materials render the Elvax 40W softer and more easily impressed and, in essence, lower the viscosity of the material. This is important when capturing details of soft tissue. Third, these materials have a tendency to relax the material when softened and to remove the memory of the material. Fourth, these materials add improved dimensional integrity to the Elvax 40W when cooled back to room temperature. Each of these vinyl acetates is discussed in greater detail below.

Polyvinyl acetate is a thermoplastic material known as chewing gum base and is manufactured by Union Carbide under the trade name of Ayab or Ayac. Polyvinyl acetate resins are available in various degrees of polymerization and in a range of molecular weights. Solution viscosity, toughness, film strength, and softening temperatures increase with ascending molecular weight. Polyvinyl acetate resins do not possess sharp softening points but become progressively softer as the temperature increases. Moreover, continued immersion in water tends to swell and soften polyvinyl acetate, particularly low-viscosity grades. Typical properties of polyvinyl acetate resins include a molecular weight of 8200 (AYAB) and 12,800 (AYAC), a softening point of 43 degrees Celsius (AYAB) and 71 degrees Celsius (AYAC), and an inherent viscosity of 0.07 g/ml (AYAB) and 0.12 g/ml (AYAC).

In the preferred embodiments, about 10% to about 40% of A-C 430 copolymer or Actol 65 is added to the Elvax-40W copolymer. The A-C 430 or Actol 65 is melt added to the Elvax 40W ethylene vinyl acetate copolymer. The heat melt composition in turn softens and relaxes the memory of the material on subsequent resoftenings. The amount of softening of the material can be altered by changing the amount of vinyl acetate modifier added to the Elvax 40. Thus, because it is possible to alter the softness of the resoftened material, the material can be modified to a grade that is suitable for muco-static, soft tissue dental impressions.

Although the above sets forth the preferred modifiers, the added vinyl acetate may be in numerous forms, including grease-like emulsions, low molecular weight grades of polyvinyl acetate, or liquid vinyl acetate monomers or powders and prills such that the principle constituent is Elvax 40W.

Figure 5:
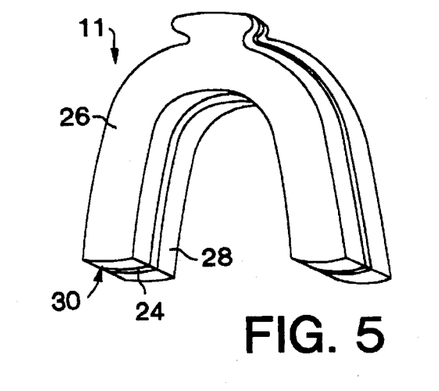
FIGS. 5 and 5A are perspective views of another embodiment of the invention illustrating a pre-formed dental impression pre-mold with the separation layer sandwiched between upper and lower layers of the inventive material.
Figure 5A:
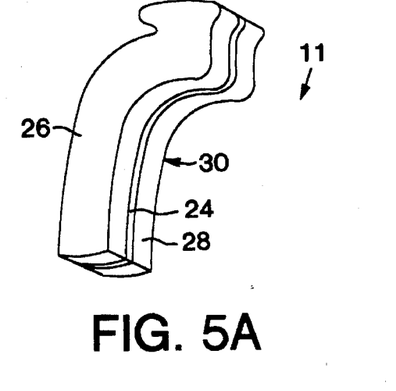
Figure 6:
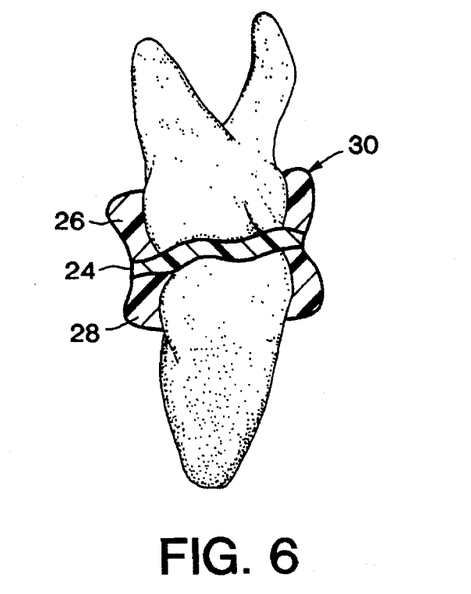
FIG. 6 is a partial side view of a dental impression mold being formed with the pre-mold of FIG. 5, illustrating its appearance as an upper and lower tooth firmly presses against the dental impression pre-mold.

In yet another embodiment, a pre-form dental impression pre-mold 11 is provided for a fixed restorative as shown in FIGS. 5, 5A and 6. This comprises a pair of ethylene vinyl acetate copolymer pre-forms 26 and 28 or modifications thereof sandwiching a second pre-form 24 made of a high molecular weight material, such as polycaprolactone. Pre-forms 26 and 28 are preferably Elvax 40W mixed with 10 to 40% by weight of Actol 65 or 10 to 40% by weight A-C 430. Pre-forms 26 and 28 are made from the same materials as pre-forms 10 described above.

The dental impression material is cooled and die cut into pieces of various sizes, shapes, and thicknesses for accommodating full, quadrant, or anterior type impressions. Next, pieces of high molecular weight polycaprolactone are die cut from a thin sheet or profile of the material. Polycaprolactone of the formula $HOR-O[C(O)(CH_2)_5]_n OH$ wherein R is aliphatic group and n is 300 to 650 and preferably has an average molecular weight of from about 35,000 to about 60,000, a crystalline melting point of from about 120° F. to about 150° F., and is commercially available from TAK Systems, Wareham, Mass. The polycaprolactone pieces are die cut to perfectly mate with and match the pieces of the extruded Elvax 40W or Elvax 40W blend. The polycaprolactone pre-form 24 is then sandwiched between two pieces of the Elvax 40W pre-form such that the Elvax 40W pieces comprise a bottom piece 26 and a top piece 28 (FIG. 5). The pieces are pre-assembled into a pre-form dental impression pre-mold 30 with heat or adhesives.

After the pieces have been assembled, the dental impression pre-mold 30 is placed into a container of water at a temperature range of about 130° F. to about 180° F. but preferably about 160° F. to 170° C. for approximately one to two minutes. At the end of this time, dental impression pre-mold 30 is removed from the water. After its removal, dental impression pre-mold 30 retains its shape and conformation, but is very soft and easy to impress. The dental impression 30 is then placed broadly onto the occlusal surface of the lower mandibular teeth of the patient wherein the patient closes into normal centric occlusion for approximately five minutes such that the upper and lower teeth firmly press against the upper and lower surfaces of the Elvax 40W pre-form. The polycaprolactone pre-form separates the upper and lower impressions from one another (FIG. 6). After approximately five minutes, the pre-mold 30 is then easily removed from the patient's mouth revealing a highly detailed and accurate dental impression mold of the upper teeth, the lower teeth, and the bite relationship of upper to lower teeth.

The dental impression mold recesses are then filled with a model material such as, for example, gypsum, to obtain a working model of the patient's arches for fabricating an appliance or dental prosthesis device.

Figure 7:
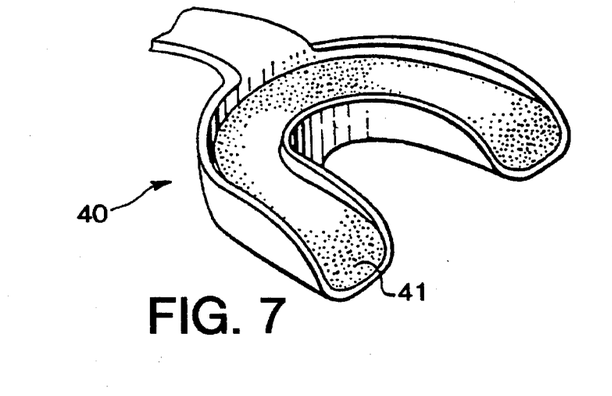
FIG. 7 is a perspective view of a dental impression tray containing the inventive dental impression material.

FIG. 7 illustrates a dental impression tray 40 which is filled with an impression material 41. The impression material contains about 25% to about 90% by weight Elvax 40W and about 10% to about 75% by weight of Actol 65 and/or A-C 430. In operation, the filled impression tray is immersed for about 30 seconds to about three minutes, in water heated to a temperature of from about 120° F. to about 170° F. The tray is removed and a dental impression is taken of the patient's teeth. The impression material is softened and allowed to set on the patient's teeth for about four to seven minutes. The dental impression material cools to less than 110° F. and hardens or sets into rubber set or rubber-like form. If the impression is not suitable for, or requires reworking, it can be corrected where necessary by heating a particular area or, it can be totally reheated to soften the entire material and allow another impression to be taken.

Figure 8:
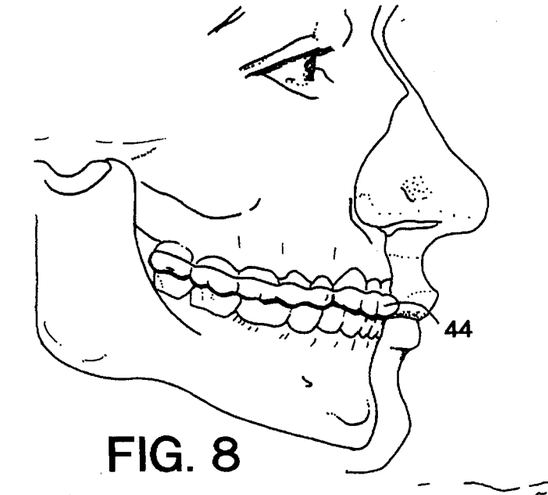
FIG. 8 is a night guard.

FIG. 8 illustrates a night guard 44 composed of my impression material as described above.

Figure 9:
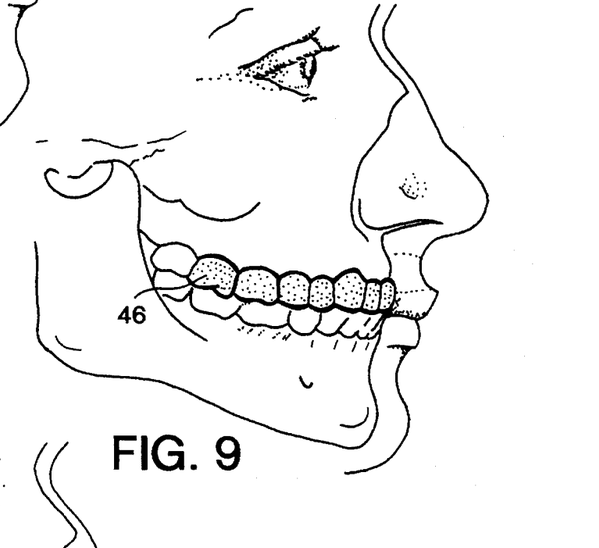
FIG. 9 is a retainer.

FIG. 9 illustrates a retainer 46 composed of my impression material as described above.

Figure 10:
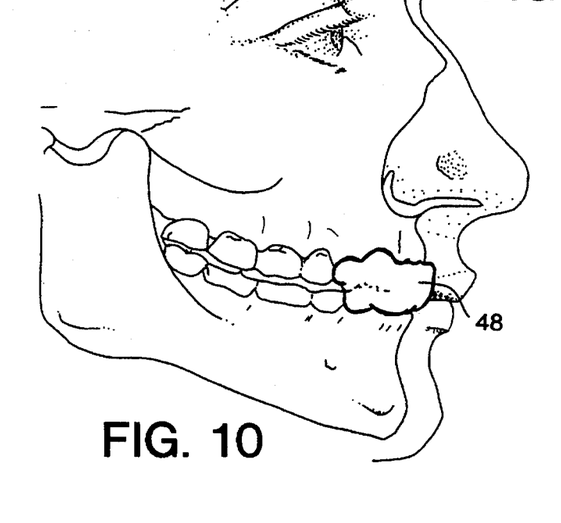
FIG. 10 is an anti-snore device.

FIG. 10 illustrates an anti-snore device 48 composed of my impression material as described above.

The night guard 44, retainer 46 and anti-snore device 48 may be prepared by using an appropriate impression tray filled with my dental impression material or a preform composed of my dental impression material may be used.

The dental impression trays may be prefilled or filled by means of a syringe.

The following examples are intended to be illustrative of the preferred embodiments of the invention and to teach one of ordinary skill in the art how to make and use the invention. These examples are not intended to limit the invention or its protection in any way.

EXAMPLE 1

A dental impression composition Was prepared by mixing 65 parts by weight of Elvax 40W and mixing 35 parts of AC 430. The composition was then melt blended in a conventional oven at a temperature of 450° F. The composition was then loaded into conventional dental impression trays and allowed to cool. The pre-loaded tray was then placed into water that was about 160° F. for one minute, then removed. The composition softened greatly. It was then placed into the mouth of the subject and pressed against the teeth and soft tissues. After five minutes, this was removed and revealed a non-distortable rubber-like dental impression of the teeth and soft tissues. This impression was preferred in those instances where the capturing of minute details of soft oral tissues is required.

EXAMPLE 2

A dental impression composition was prepared by mixing 62 parts by weight of Elvax 40W together with 38 parts of Actol 65. The composition was then melt blended in a conventional oven and utilized as in Example No. 1. The results were similar and provided an acceptable dental impression with an emphasis on soft tissue detail.

EXAMPLE 3

A dental impression composition was prepared by mixing 70 parts by weight of Actol 65 and 35 parts of Elvax 40W. This mixture was melt blended in a conventional oven and loaded into plastic syringes having a mouth diameter opening of about ⅜". The loaded syringes were allowed to cool to room temperature where the mixture hardened. The pre-loaded syringes were then placed into water at a temperature of 170° F. for four minutes to place the composition in a flowable Condition. The contents of the syringes were then ejected into a conventional dental impression tray and inserted into the open mouth of the subject and pressed against the teeth. This was removed after five minutes revealing a highly detailed and accurate impression, however, this impression, although acceptable, was less rubber-like and subject to tearing.

EXAMPLE 4

A dental impression composition was prepared by melting Elvax grade 40W in an extrusion hopper. The melt was then subjected to high shear force and extruded under pressure through a restricted die opening to produce 3/16" sheets. The sheet composition was cooled and cut into quadrant size pre-forms. A pre-form was placed into water at a temperature of 160° F. for one minute then removed and placed on the occlusal surface of the subject's teeth. The subject was instructed to close fully into a normal centric relation. After five minutes, the pre-form was removed and revealed a very accurate and detailed bite registration impression. This composition was not suitable for soft tissue detail.

EXAMPLE 5

A dental impression pre-form was prepared by mixing 78 parts by weight of Elvax 40W with 22 parts by weight of Actol 65 prills, then extruded and formed into a flat, semi-circular shape approximately 3/16 inch thick.

The pre-form was placed in water that was about 160° F. for one minute and then removed form the hot water. The pre-form was soft, but maintained its shape and was placed onto the occlusal surface of the lower mandibular teeth of a subject. The pre-form was held in his mouth for about five minutes. The pre-form hardened and was easily removed from the subject's mouth. The hardened pre-form revealed a non-distortable rubber-like functional dental impression of the upper teeth, the lower teeth, and the relationship of the upper and lower teeth to one another.

EXAMPLE 6

A pre-form dental impression pre-mold 30 was prepared from two approximately 3/16 inch thick Elvax 40W and Actol 65 pre-forms 26 and 28 made according to Example 1. The second pre-form membrane was made of a thin separator film sheet of a high molecular weight polycaprolactone which was also molded into a flat, semi-circular shape. The second pre-form was then sandwiched between the two pre-forms 26 and 28 to form the pre-mold 30.

The pre-form dental impression pre-mold 30 was placed in water that was about 160° F. for one minute and then removed form the hot water and placed onto the occlusal surface of the lower mandibular teeth of a subject. The subject held the pre-form in his mouth for five minutes. The pre-form hardened and was easily removed from the subject's mouth and revealed a non-distortable rubber like dental impression mold of the upper teeth, the lower teeth, and the relationship of the upper and lower teeth to one another.

This dental impression mold was then filled with gypsum in order to obtain a working model of the subject's arches.

EXAMPLE 7

Examples 5 and 6 were repeated using about 20 parts by weight of AC 430 instead of Actol 65. The results were similar and provided acceptable dental impression pre-forms and pre-molds. However, the use of AC 430 grease-like composition was difficult to extrude and the resulting pre-form and premolds did not have the same versatile handling properties as the Actol 65 extruded pre-form and pre-molds. [See Examples 4, 5, and 6].

Therefore, it should be recognized that, while the invention has been described in relation to a preferred embodiment thereof, those skilled in the art may develop a wide variation of structural details without departing form the principles of the invention. Accordingly, the appended claims are to be construed to cover all equivalents falling within the scope and spirit of the invention.

The invention claimed is:

1. A dental impression composition comprising an ethylene vinyl acetate copolymer and said composition having a softening point of about 120° F. to about 170° F. and being hard at a temperature of 110° F. and a vinyl acetate modifier polymer selected from the group consisting of a second ethylene vinyl acetate, ethylene vinyl acetate vinyl alcohol ester, vinyl acetate, polyvinyl acetate, and mixtures thereof.

2. The dental impression composition of claim 1 wherein said ethylene vinyl acetate copolymer has a vinyl acetate content of about 30% to about 45% by weight.

3. The dental impression composition of claim 2 wherein said composition is extruded.

4. The dental impression composition of claim 1 wherein said polymer modifier is ethylene vinyl acetate vinyl alcohol ester having a melting range of 40° to 65° C., an average molecular weight of 2400, a hydroxyl number of 85–120, and a melt index of 48–66 dg/min.

5. The dental impression composition of claim 4 wherein said composition is extruded.

6. The dental impression composition of claim 1 wherein said polymer modifier is said second ethylene vinyl acetate having a vinyl acetate content of 23–30% by weight, a hardness of 40–100 dmm and viscosity at 140° C. of about 600 cps.

7. The dental impression composition of claim 6 wherein said composition is extruded.

8. A dental impression pre-form prepared from a composition containing an ethylene vinyl acetate copolymer and said composition having a softening point of about 120° F. to about 170° F. and being hard at a temperature of 110° F. and a vinyl acetate polymer modifier selected from the group consisting of a second ethylene vinyl acetate, ethylene vinyl acetate vinyl alcohol ester, vinyl acetate, polyvinyl acetate and mixtures thereof.

9. The dental impression pre-form of claim 8 wherein said ethylene vinyl acetate copolymer has a vinyl acetate content of about 30% to about 45% by weight.

10. The dental impression pre-form of claim 9 wherein said composition is extruded.

11. The dental impression pre-form of claim 8 wherein said polymer modifier is ethylene vinyl acetate vinyl alcohol ester having a melting range of 40° to 65° C., an average molecular weight of 2400, a hydroxyl number of 85–120, and a melt index of 48–66 dg/min.

12. The dental impression pre-form of claim 11 wherein said composition is extruded.

13. The dental impression pre-form of claim 8 wherein said polymer modifier is said second ethylene vinyl acetate has a vinyl acetate content of about 23% to about 30% by weight, a hardness of 40–100 dmm and a viscosity at 140° C. of about 600 cps.

14. The dental impression pre-form of claim 13 wherein said composition is extruded.

15. A dental impression preform comprising:
 a first and second dental impression pre-form made of an vinyl acetate copolymer composition, and
 a separator sheet sandwiched between and attached to said first and second pre-form, said separator sheet made of a high molecular weight polycaprolactone.

16. The dental impression pre-form of claim 15 wherein said vinyl acetate copolymer is ethylene vinyl acetate.

17. The dental impression pre-form of claim 16 wherein said ethylene vinyl acetate copolymer has a vinyl acetate content of about 30% to about 45% by weight vinyl acetate.

18. The dental impression pre-form of claim 17 wherein said vinyl acetate composition further comprises a vinyl acetate polymer modifier selected from the group consisting of a second ethylene vinyl acetate, ethylene vinyl acetate vinyl alcohol ester, vinyl acetate, polyvinyl acetate and mixtures thereof.

19. The dental impression pre-form of claim 18 wherein said polymer modifier is ethylene vinyl acetate vinyl alcohol ester having a melting range of 40° to 65° C., an average molecular weight of 2400, a hydroxyl number of 85–120, about 39% to about 42% by weight vinyl acetate and a melt index of 48–66 dg/min.

20. The dental impression pre-form of claim 19 wherein said composition is extruded.

21. The dental impression pre-form of claim 18 wherein said vinyl acetate polymer modifier is said second ethylene vinyl acetate which has a vinyl acetate content of about 23% to about 30% by weight and a hardness of 40–100 dmm.

22. The dental impression pre-form of claim 21 wherein said composition is extruded.

23. The dental impression pre-form of claim 17 wherein said composition is extruded.

24. A dental impression tray comprising an impression tray filled with a dental impression composition having at least one vinyl acetate copolymer wherein the composition softens at a temperature of from about 120° F. to about 170° F. to permit it being used as a dental impression composition and which hardens to a non-distortable rubber-like dental impression at a temperature of from about 90° F. to about 110° F.

25. The dental impression tray of claim 24 wherein the dental impression tray is a disposable dental impression tray.

26. The dental impression tray of claim 24 or 25 wherein said vinyl acetate copolymer is ethylene vinyl acetate.

27. The dental impression tray of claim 26 wherein said ethylene vinyl acetate copolymer has a vinyl acetate content of about 30% to about 45% by weight.

28. The dental impression tray of claim 24 or 25 wherein said vinyl acetate copolymer is an ethylene vinyl acetate copolymer having a vinyl acetate content of about 30% to about 45% by weight.

29. The dental impression tray of claim 28 wherein said composition is an extruded composition.

30. The dental impression tray of claim 24 or 25 wherein said composition also contains a vinyl acetate modifier polymer selected from the group consisting of a second ethylene vinyl acetate, ethylene vinyl acetate vinyl alcohol ester, vinyl acetate, polyvinyl acetate, and mixtures thereof.

31. The dental impression tray of claim 30 wherein said vinyl acetate modifier polymer is ethylene vinyl acetate vinyl alcohol ester having a melting range of 40° to 65° C., an average molecular weight of 2400, a hydroxyl number of 85–120, and a melt index of 48–66 dg/min.

32. The dental impression tray of claim 31 wherein said composition is an extruded composition.

33. The dental impression tray of claim 31 wherein said vinyl acetate copolymer is an ethylene vinyl acetate copolymer has a vinyl acetate content of about 30% to about 45% by weight.

34. The dental impression tray of claim 24 or 25 wherein said polymer modifier is said second ethylene vinyl acetate having a vinyl acetate content of 23–30% by weight, a hardness of 40–100 dmm and viscosity at 140° C. of about 600 cps.

35. The dental impression tray of claim 34 wherein said composition is an extruded composition.

36. The dental impression tray of claim 34 wherein said vinyl acetate copolymer is an ethylene vinyl acetate copolymer has a vinyl acetate content of about 30% to about 45% by weight.

37. A functional dental impression device comprising said device being prepared from an ethylene vinyl acetate copolymer and said device having a softening point of about 120° F. to about 170° F. and being hard at a temperature of 110° F. and a vinyl acetate modifier polymer selected from the group consisting of a second ethylene vinyl acetate, ethylene vinyl acetate vinyl alcohol ester, vinyl acetate, polyvinyl acetate, and mixtures thereof.

38. The functional dental impression device of claim 37 wherein said ethylene vinyl acetate copolymer has about 30% to about 45% by weight vinyl acetate.

39. The functional dental impression device of claim 38 wherein said composition is extruded.

40. The functional dental impression device of claim 37 wherein said polymer modifier is ethylene vinyl acetate vinyl alcohol ester having a melting range of 40° to 65° C., an average molecular weight of 2400, a hydroxyl number of 85–120, about 39 to 42% by weight vinyl acetate and a melt index of 48–66 dg/min.

41. The functional dental impression device of claim 40 wherein said polymer modifier is said second ethylene vinyl acetate having a vinyl acetate content of 23–30% by weight, a hardness of 40–100 dmm and viscosity at 140° C. of about 600 cps.

42. The functional dental impression device of claim 41 wherein said composition is extruded.

43. The functional dental impression device of claim 40 wherein said composition is extruded.

44. A method for taking a dental impression comprising the steps of:

placing an ethylene vinyl acetate copolymer dental impression pre-form into a container of water that is heated to a temperature of from about 120° F. to about 170° F. and said ethylene vinyl acetate copolymer having about 30% to about 40% by weight vinyl acetate and including with said ethylene vinyl acetate a vinyl acetate polymer modifier selected from the group consisting of a second ethylene vinyl acetate, ethylene vinyl acetate vinyl alcohol ester, vinyl acetate, polyvinyl acetate and mixtures thereof:

soaking said pre-form in said container of water for about 30 seconds to about 2 minutes to soften said dental impression pre-form;

removing the softened dental impression pre-form from said container of water and placing said softened dental impression pre-form onto the occlusal surface of the teeth;

pressing the softened dental impression pre-form onto the teeth to form an impression of the teeth on the pre-form, holding this position on the teeth until the pre-form hardens; and removing said pre-form from the teeth to reveal a highly detailed and accurate dental impression of the teeth.

45. The method of claim 44 wherein said ethylene vinyl acetate copolymer has about 30% to about 45% by weight vinyl acetate.

46. The method of claim 45 wherein said composition is an extruded composition.

47. The method of claim 44 wherein said vinyl acetate polymer modifier compound is said ethylene vinyl acetate vinyl alcohol ester having a melting range of 40° to 65° C., an average molecular weight of 2400, hydroxyl number of 85–120, about 39% to about 42% by weight vinyl acetate and a melt index of 48–66 dg/min.

48. The method of claim 47 wherein said composition is an extruded composition.

49. The method of claim 44 wherein said vinyl acetate polymer modifier is said second ethylene vinyl acetate having a vinyl acetate content of about 23% to about 30% by weight, a hardness of 40–100 dmm and a viscosity at 140° C. of 600 cps.

50. The method of claim 49 wherein said composition is an extruded composition.

51. The method of any one of claims 44 to 50 wherein the pre-form is soaked in the container of heated water for about one minute and held on the teeth for less than seven minutes.

* * * * *